United States Patent
Child et al.

(10) Patent No.: US 6,283,952 B1
(45) Date of Patent: *Sep. 4, 2001

(54) SHAPED TAMPON

(75) Inventors: William M. Child, Monson; Warren Tarr, Turners Falls, both of MA (US)

(73) Assignee: Tambrands, Inc., Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 550 days.

(21) Appl. No.: 08/851,381

(22) Filed: May 5, 1997

Related U.S. Application Data

(63) Continuation of application No. 07/998,700, filed on Dec. 30, 1992, now abandoned.

(51) Int. Cl.[7] .............. A61M 1/00; A61F 13/15; A61F 13/20
(52) U.S. Cl. .............. 604/540; 604/11; 604/380; 604/385.01; 604/904; 28/118; 28/119; 28/120
(58) Field of Search .................... 604/904, 380, 604/11–15, 540, 385.01; 28/118–120

(56) References Cited

U.S. PATENT DOCUMENTS

| | | | |
|---|---|---|---|
| 2,188,923 | 2/1940 | Robinson . | |
| 2,620,799 * | 12/1952 | Ganz | 604/904 |
| 2,926,394 * | 3/1960 | Bletzinger et al. | 28/120 |
| 3,131,435 | 5/1964 | Cloots et al. | 28/119 |
| 3,422,496 * | 1/1969 | Wolff et al. | 28/118 |
| 3,595,236 * | 7/1971 | Corrigan | 604/904 |
| 3,683,912 | 8/1972 | Olson et al. . | |
| 3,699,965 | 10/1972 | Dostal | 604/904 |
| 3,710,420 * | 1/1973 | Yamauchi | 28/120 |
| 3,731,687 | 5/1973 | Glassman | 604/904 |
| 3,738,364 * | 6/1973 | Brien et al. | 604/904 |
| 3,812,856 * | 5/1974 | Duncan et al. | 604/904 |
| 3,854,481 | 12/1974 | Messing . | |
| 3,946,737 | 3/1976 | Kobler | 604/904 |
| 3,971,378 | 7/1976 | Krantz | 604/904 |
| 3,976,075 * | 8/1976 | Chinai et al. | 604/904 |
| 3,983,875 * | 10/1976 | Truman | 604/904 |
| 4,027,673 | 6/1977 | Poncy et al. | 604/904 |
| 4,169,004 | 9/1979 | Kock et al. . | |
| 4,200,101 * | 4/1980 | Glassman | 604/904 |
| 4,212,301 | 7/1980 | Johnson . | |
| 4,222,381 | 9/1980 | Widlund et al. . | |
| 4,274,412 | 6/1981 | Austin . | |
| 4,335,720 * | 6/1982 | Glassman | 604/904 |
| 4,341,214 | 7/1982 | Fries et al. . | |
| 4,374,522 | 2/1983 | Olevsky . | |
| 4,563,398 | 1/1986 | Sustmann | 428/542.8 |
| 4,642,108 | 2/1987 | Sustman | 604/379 |
| 4,743,237 | 5/1988 | Sweere | 604/358 |
| 4,775,377 | 10/1988 | Sweere | 604/904 |
| 5,004,467 | 4/1991 | Hinzmann et al. | 604/904 |
| 5,350,371 * | 9/1994 | Van Iten | 604/904 |
| 5,688,257 * | 11/1997 | Olsen | 28/118 |
| 5,813,102 * | 9/1998 | Leutwyler et al. | 28/118 |

FOREIGN PATENT DOCUMENTS

| 2 211 096 | 6/1989 | (GB) . |
| 90/07159 | 6/1991 | (WO) . |

* cited by examiner

*Primary Examiner*—John G. Weiss
*Assistant Examiner*—K. M. Reichle
(74) *Attorney, Agent, or Firm*—Matthew P. Fitzpatrick; Kevin C. Johnson; Steven W. Miller

(57) ABSTRACT

The invention provides an improved tampon, particularly suited for use as a digital tampon, having a portion of fibers at a withdrawal end of the tampon displaced towards an insertion end, causing a fiber density in the vicinity of the withdrawal end to be lower than an average fiber density of the tampon. The tampon also includes an indentation in the withdrawal end. In combination, the lower fiber density of the withdrawal end and the indentation in the withdrawal end cause the withdrawal end to be soft and readily flareable. When the tampon is provided with an overwrap the indentation also allows excess overwrap at the withdrawal end to be tucked into the tampon, improving the aesthetic qualities of the tampon and facilitating digital insertion.

7 Claims, 4 Drawing Sheets

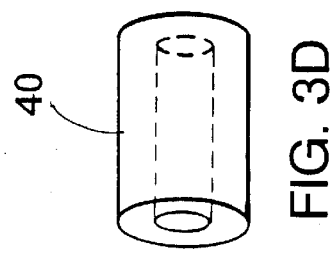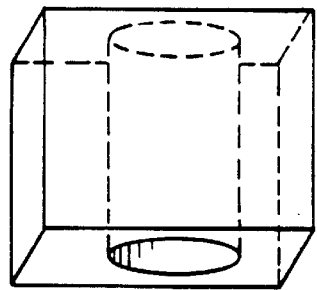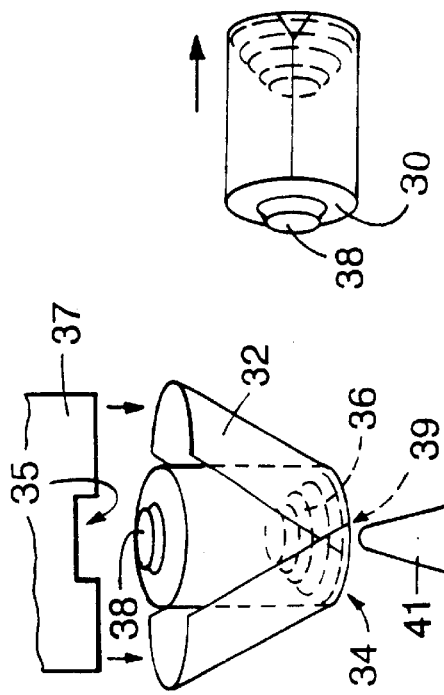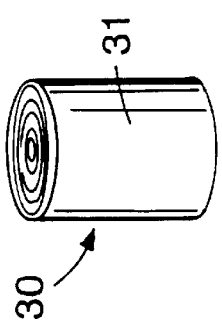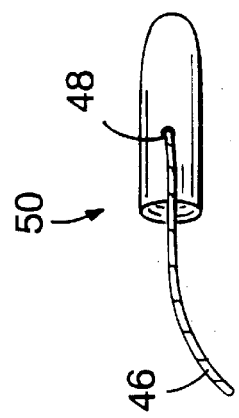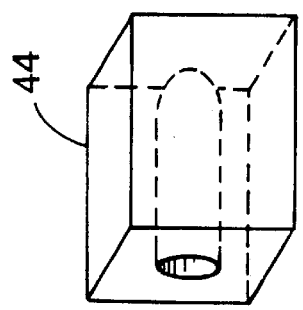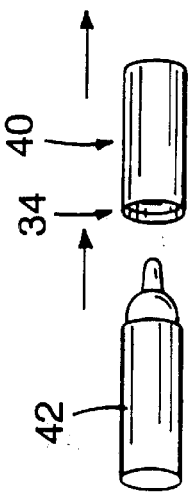

SHAPED TAMPON

This is a continuation of application Ser. No. 07/998,700, filed Dec. 30, 1992, now abandoned.

BACKGROUND OF THE INVENTION

The present invention relates to tampons.

Tampons for use in absorption of menstrual flow have typically been inserted using an applicator, as is well known. However, more recently, "digital" tampons have been developed, i.e., tampons which are inserted manually by the user, without the need for an applicator, thereby eliminating waste and providing a smaller, more compact product.

Most digital tampons are produced from rolled or spirally wound pledgets. Generally, the withdrawal cord of the tampon is rolled into the pledget and extends from the center of the withdrawal end. When the withdrawal cord is attached in this manner, the user can "flare" the withdrawal end of the tampon prior to insertion, to provide a well for the user's finger, by holding the tampon and pulling the cord against the periphery of the withdrawal end.

When the withdrawal cord is rolled into the pledget, however, the tampon may "telescope" when withdrawn, i.e., the central windings may be pulled out of the wound tampon. Accordingly, an alternate method of cord attachment was developed, in which the withdrawal cord is punched through the pledget, e.g., as disclosed in U.S. Pat. No. 5,004,467. These tampons, while eliminating the problem of telescoping, typically cannot be flared by the user, making insertion more difficult.

Digital tampons typically include an overwrap on the tampon to prevent fiber fluff-off and ease insertion. Conventional methods of overwrapping tampons, e.g., that disclosed in U.S. Pat. No. 5,004,467, leave excess, baggy overwrap at the tampon base after compression of the pledget, increasing the difficulty of insertion, and reducing the aesthetic qualities of the product.

SUMMARY OF THE INVENTION

The present invention provides an improved tampon, particularly suited for use as a digital tampon.

In one aspect, the invention features a digital tampon which includes an elongated pledget formed of absorbent material that has been radially compressed, and a withdrawal cord attached to the pledget. The pledget has, at one end, an insertion end shaped for insertion into a body cavity, and, at the other end, a withdrawal end shaped to permit the user to apply an axial force thereto for inserting the tampon. The fiber density of the pledget in the vicinity of the withdrawal end is lower than the average fiber density of the pledget. The reduced fiber density of the withdrawal end allows the user to easily flare the soft withdrawal end, providing a well for digital insertion.

The tampon of the invention preferably also includes an indentation in the compressed pledget, extending axially from the withdrawal end into the interior of the pledget. This indentation further facilitates flaring, provides a finger well for the user even if the user does not flare the withdrawal end, and allows excess overwrap at the withdrawal end of the tampon to be tucked in. Preferably, the indentation comprises a substantially hemispherical region nearest the withdrawal end followed by a substantially conical region further from the withdrawal end.

In a second aspect, the invention features a tampon in which, prior to compression, radially central portions of the absorbent material are displaced at the withdrawal end in an axial direction toward the insertion end, resulting in increased fiber density in at least some locations along the central region of the tampon. This higher fiber density provides a firmer, denser central core for transferring force between a pushrod (applied to the withdrawal end) and a header (applied to the insertion end) during the head-forming operation in a tampon manufacturing process. This improved transfer of force allows formation of more elongated head shapes which are difficult to form on conventional tampons; e.g., the length of the head can be made at least 75% (and more preferably more than 100%) of the diameter of the pledget. The invention also provides a more stable head. Head formation is accomplished with a lower average fiber density than with conventionally formed pledgets, providing a softer tampon with a greater absorbant efficiency.

The tampon of the invention can thus be made softer than conventional tampons, allowing the tampon to expand more easily and provide higher absorbency. The high absorbency of the tampon, in turn, allows a lower tampon weight for a given absorbency.

In preferred embodiments, the tampon is constructed by rolling a layer of absorbent material. During the above mentioned displacement of central portions of the uncompressed tampon, some central layers of material are displaced to some degree throughout the length of the pledget and project outwardly at the insertion end, to give a rounded shape to the insertion end. The tampon further includes a permeable overwrap material surrounding at least a portion of the pledget.

In another aspect, the invention relates to a method of forming a digital tampon, having an insertion end shaped for insertion into a body cavity, a withdrawal end shaped to permit the user to apply an axial force thereto for inserting the tampon, and having a cord attached thereto for withdrawal from the cavity. The method includes the steps of: (a) rolling a length of compressible absorbent material to form a pledget with one end corresponding to the withdrawal end and another end corresponding to the, insertion end, (b) displacing radially central layers of the absorbent material from the withdrawal end of the pledget towards the insertion end, (c) radially compressing the pledget, and (d) forming an indentation in the withdrawal end of the compressed pledget".

In preferred embodiments, the indentation is formed by a pushrod having an elongated, substantially conical member extending from a substantially hemispherical base.

In another aspect, the invention features a tampon formed using a method of the invention.

Other features and advantages of the invention will be apparent from the following description of the preferred embodiments and from the claims.

BRIEF DESCRIPTION OF THE DRAWINGS

FIGS. 3A–3F are a schematic flow diagram of a process for forming a tampon according to one embodiment of the invention.

DESCRIPTION OF THE PREFERRED EMBODIMENTS

Figure 1:
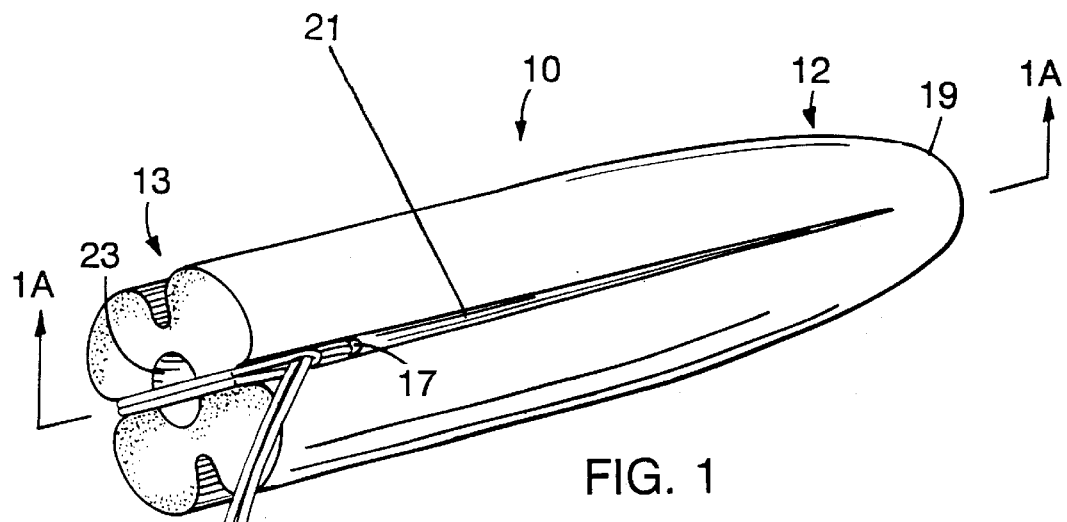
FIG. 1 is a perspective view of a tampon according to one embodiment of the invention.
Figure 1A:
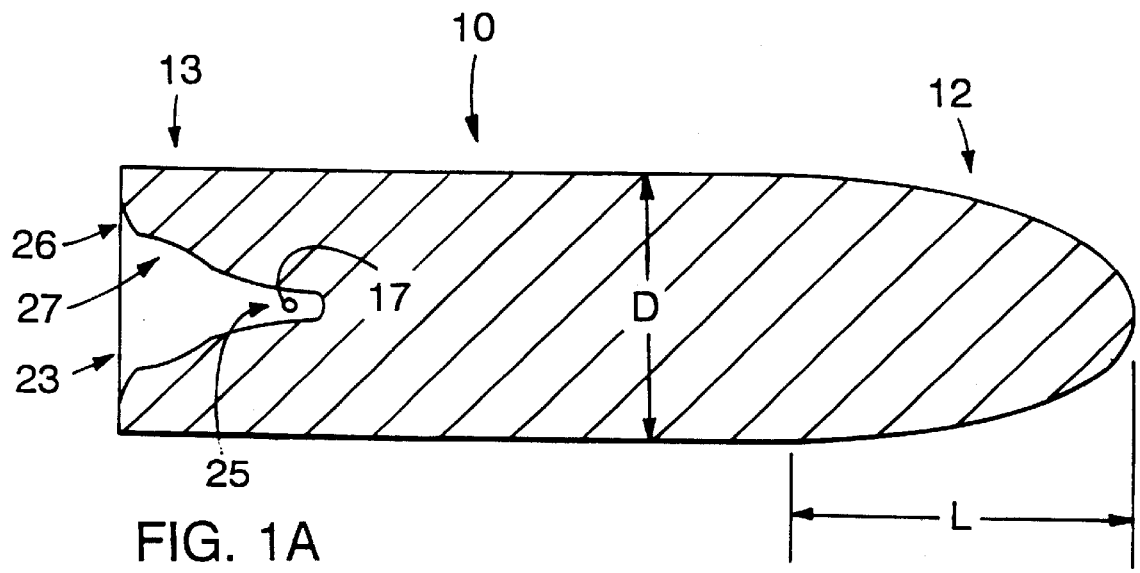
FIG. 1A is a cross-sectional view of the tampon of FIG. 1, taken along line 1A—1A.

Referring to FIGS. 1 and 1A, a tampon 10 is shown in the condition in which it would be sold to a consumer. Tampon 10 includes insertion end 12, withdrawal end 13, and withdrawal cord 15. Withdrawal cord 15 is threaded through aperture 17 which extends transversely through the tampon, through opposing longitudinal compression indentations 21. Withdrawal cord 15 is fastened with a slip knot, which is located in indentation 21, rather than at the base of the tampon, for optimal flarability. Insertion end 12 preferably has a smooth, elongated head 19, with head length L (FIG. 1A) approximately 150% of pledget diameter D. This provides an elliptical or "bullet" shape for optimal ease of insertion. Other head shapes may be used in some aspects of the invention, e.g., conventional domed head shapes (in which head length L is only 50% of diameter D). The tampon also preferably includes longitudinal compression indentations 21.

An axial indentation 23 is defined in the withdrawal end 13 of the tampon. A preferred shape for this indentation is shown in FIG. 1A. As shown, the indentation comprises a substantially conical region 25, terminating at the withdrawal end in a substantially hemispherical region 27. Conical region 25 allows the indentation to extend further into the interior of the tampon than would be possible if the indentation were entirely hemispherical, thereby improving the softness of the withdrawal end. Conical region 25 also allows excess overwrap material at the withdrawal end to be securely tucked in. Hemispherical region 27 provides a finger indent or well which is better dimensioned for a user's finger than if the indentation were entirely conical. Taper region 26, around the circumference of the hemispherical region, results from the outer layers of the rolled pledget being pulled inward by the adjoining inner layers as the inner layers are displaced.

Figure 2:
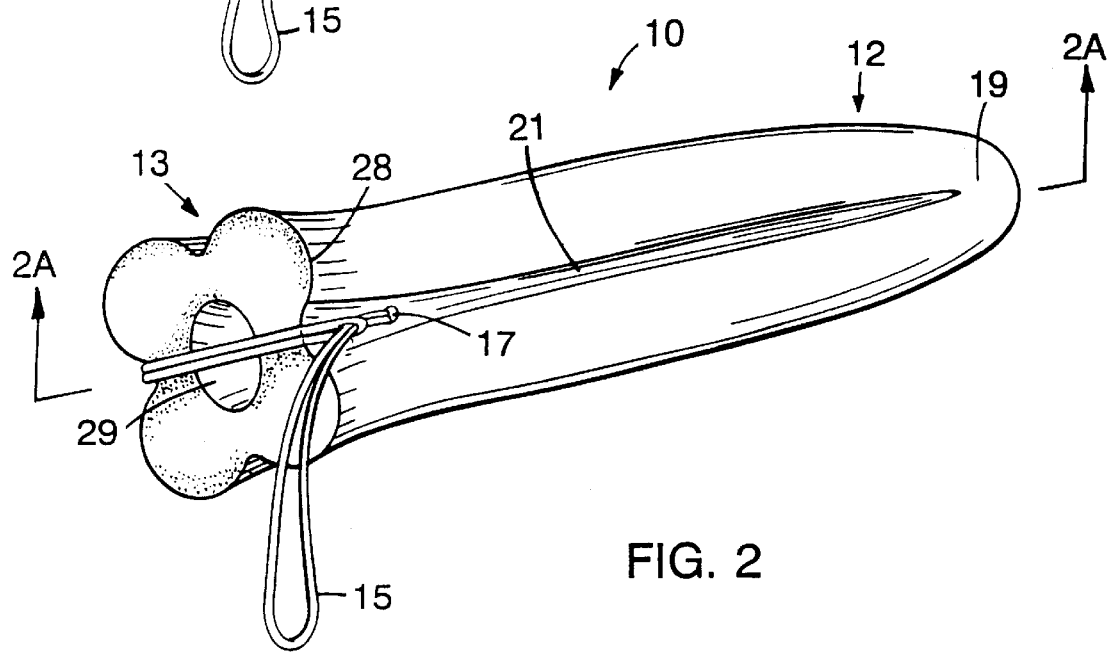
FIG. 2 is a perspective view of the tampon of FIG. 1 after flaring.
Figure 2A:
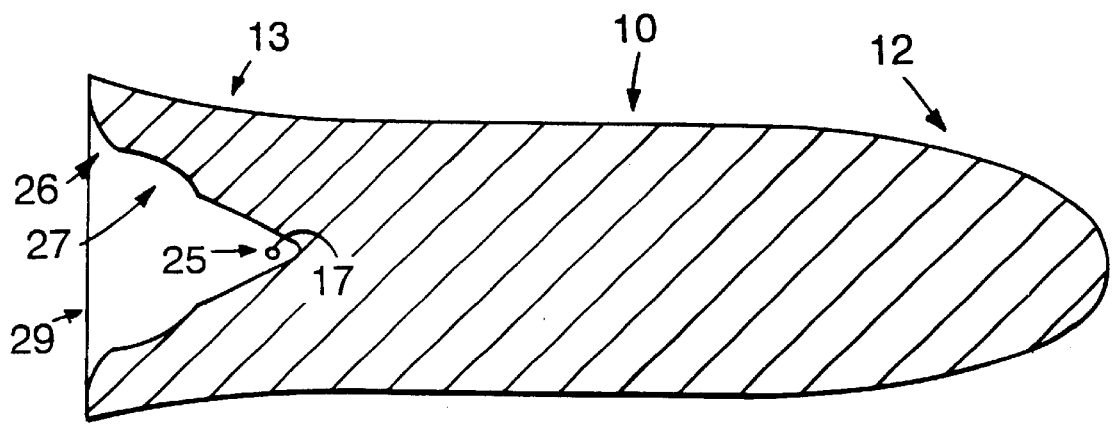
FIG. 2A is a cross-sectional view of FIG. 2, taken along line 2A—2A.

Referring to FIGS. 2 and 2A, the tampon of FIGS. 1 and 1A is shown after flaring. The absorbent material at the withdrawal end has been spread out by the user, forming a flare 28, and the indentation has expanded to provide a finger indent 29. The user is thus provided with a large, soft area for digital insertion.

Any conventional absorbent material is suitable for use in the tampon of the invention. Preferred absorbent materials are selected from the group consisting of cellulosic fibers, cotton fibers, rayon fibers and blends thereof. The fiber density of the absorbent material is greater in the vicinity of the insertion end than in the vicinity of the withdrawal end, so that the withdrawal end is soft and easy to manipulate, while the insertion end is hard and stable for ease of manufacturing (head forming) and comfortable insertion. This density differential is preferably accomplished by displacing a portion of the absorbent material of the uncompressed pledget from the withdrawal end toward the insertion end.

A preferred method of forming a tampon of the invention is shown schematically in FIGS. 3A–3F. First, an uncompressed pledget 30 of rolled absorbent material 31 is provided (FIG. 3A). The pledget can be rolled using conventional winding equipment, e.g. those available from Karl Ruggli AG, Fisibach, Switzerland, or the FALU machine made by K. Fassbind-Ludwig & Co., Fulu Machinbau, Wagen Bei Jona, Switzerland.

Next, a sheet of overwrap material 32 is placed adjacent a first end 34 of the pledget, and folded around a portion of the pledget (FIG. 3B), preferably in the form of an envelope as described in U.S. Pat. No. 5,004,467, the disclosure of which is incorporated herein by reference. The overwrap material may be a permeable thermoplastic, e.g., polypropylene, polyethylene, or blends thereof, or may be a fabric or a non-woven. (If a tampon without overwrap is desired, this step may be omitted.)

Figure 4:
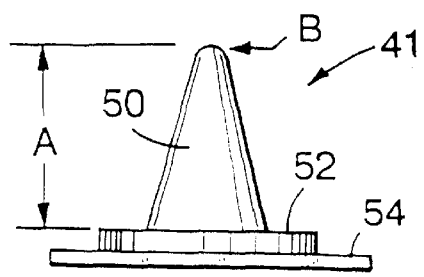
FIG. 4 is a side plan view of a conical member according to one embodiment of the invention.
Figure 4A:
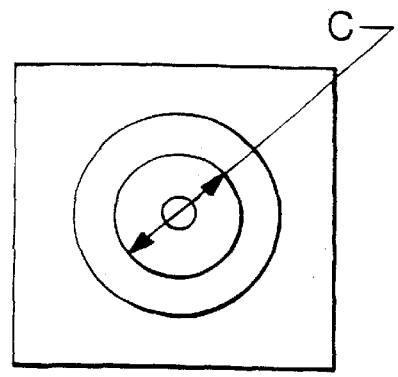
FIG. 4A is a top plan view of the conical member of FIG. 4.
Figure 6:
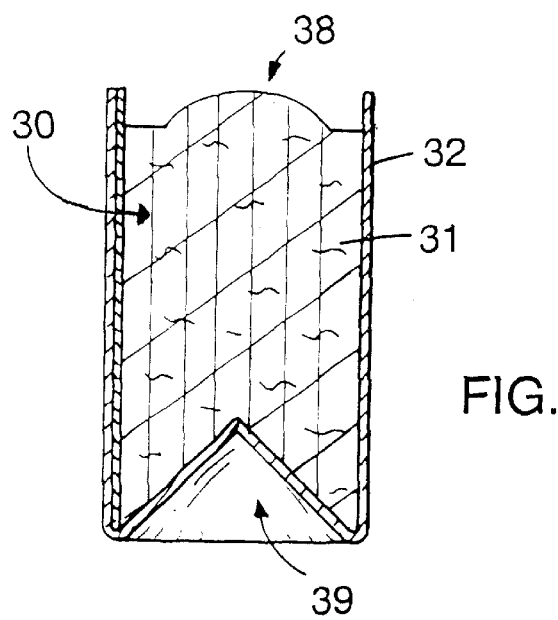
FIG. 6 is a cross-sectional view of an uncompressed pledget after the processing step shown in FIG. 3B.

Referring again to FIG. 3B, a portion 36 of the absorbent material at the first end is displaced by pressing the pledget onto a conical die 41, shown in detail in FIGS. 4 and 4A, or, alternatively, by pressing the conical die into the pledget. The displacement of material at the first is end creates a conical depression 39 in the first end. The pledget may be pressed onto the conical die simultaneous with formation of the overwrap envelope, as shown, or after formation of the envelope. Preferably, at least a portion of the opposite end of the pledget is unrestrained during this step, e.g., by providing a cavity 35 in the ram 37 which urges the pledget against the conical die, as shown, to allow material 38 at the opposite end to be pushed up by the material which is being displaced. More preferably, about one third of the volume which is displaced from the first end is allowed to be pushed up at the opposite end. This pushed up material generally aids in head formation. A cross-sectional view of an uncompressed pledget, subsequent to application of the overwrap and formation of the depression, is shown in FIG. 6.

The pledget together with overwrap, if an overwrap is included, is next compressed (FIG. 3C) and heat conditioned (FIG. 3D) in a conventional manner. Compression pressures are well known in the art. Heat conditioning time and temperature will be determined based on head formation requirements, the moisture of the absorbent material used, production speed constraints, whether an overwrap material is used, and, if so, what type of overwrap material. Optimal time and temperature can be readily determined by one skilled in the art.

The compressed pledget 40 is then pressed, using a pushrod 42 (shown in detail in FIG. 5) dimensioned to produce an indentation in the pledget, against a head-forming heated die 44 (FIG. 3E). What was the first end 34 of the uncompressed pledget (the end from which material was displaced) is pressed by the pushrod, while the opposite end contacts the die. If there is excess overwrap material at the first end of the pledget after compression, this step will cause the excess to be tucked into the indentation formed by the pushrod. This head formation step is facilitated by the displacement of the fibers in the withdrawal end towards the insertion end (FIG. 3B). Fiber displacement causes the fiber density to be increased along the central core of the pledget, giving the pushrod a firmer area to push against than it would have in a compressed pledget which was not subjected to this fiber displacement. Thus, force is translated better between the pushrod and the head-forming die, allowing the formation of more acute angles, e.g., formation of bullet shaped heads. Less axial force is needed to achieve a given head elongation, and thus a softer tampon results.

Finally, a withdrawal cord 46 is punched through a transverse aperture 48 in the compressed pledget (FIG. 3F), and secured, e.g., using a slip knot, to form the finished tampon 50.

Figure 5:
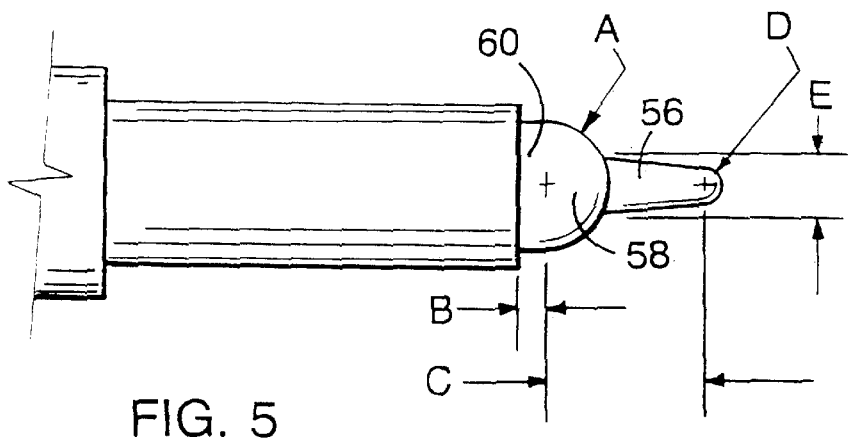
FIG. 5 is a side plan view of a push-rod according to one embodiment of the invention.

Steps 3b–3f may be accomplished using a machine commercially available from Hauni Machines, Richmond, Va., under the tradename TAMPOMAT D-500, modified to include the conical die 41 of the invention and to replace the standard Hauni pushrod, which has a flat or concave end, with a pushrod of the invention, e.g., the pushrod shown in FIG. 5, dimensioned to form an indentation in the withdrawal end.

A preferred conical die 41 for use in the displacement step (see FIG. 3B) is shown in FIGS. 4 and 4A. Conical die 41 includes conical portion 50, disk 52, and base 54, upon which the disk and conical portion are mounted. Conical portion 50 forms depression 39 shown in FIG. 3B. Disk 52 acts as a guide for positioning the conical die in the Hauni TAMPOMAT machine. If different machinery is used, a different type of guide could be used, as appropriate. Base 54 serves to hold the die in the Hauni machine, and thus, like disk 52, may not be necessary, depending upon the type of production machinery used. Typical dimensions of the die are as follows: A, the height of the conical portion, from about 0.5 to 1.25 inch; B, the radius of curvature of the conical portion, about 0.125 inch; and C, the diameter of the base of the conical portion, from about 0.80 to 1.40 inch.

A preferred pushrod 42, for use in the indentation step (see FIG. 3E) is shown in FIG. 5. Pushrod 42 preferably comprises conical portion 56 and hemispherical portion 58, which form, respectively, conical region 25 and hemispherical region 27 in the compressed pledget, as shown in FIG. 1A. Hemispherical portion 58 optionally is mounted on cylindrical base 60. Preferred dimensions of the pushrod are as follows: A, the radius of curvature of the hemispherical portion, from 0.10 to 0.20 inch; B, the height of the cylindrical base, about 0.05 inch; C, the height of the pushrod from the base of the hemispherical portion to the base of the hemispherical tip of the conical portion, from 0.30 to 0.60 inch; D, the radius of curvature of the tip of the conical portion, about 0.040 inch; and E, the diameter of the conical portion at its base, from 0.075 to 0.150 inch (this dimension will typically vary with the diameter of the hemispherical portion). The maximum diameter of the hemispherical portion is limited by the diameter of the compressed pledget, typically about 15 to 40 percent smaller.

While preferred embodiments have been described above, other variations and modifications are within the claims.

What is claimed is:

1. A method of forming a tampon intended for digital insertion, said tampon having an axial dimension oriented in an axial direction, a radial dimension oriented in a radial direction, an insertion end dimensioned for insertion into a body cavity, a withdrawal end, and a cord attached thereto for withdrawal from the cavity, said method comprising the steps of:
    (a) rolling a length of compressible absorbent material into a rolled layered pledget with one end corresponding to the withdrawal end and another end corresponding to the insertion end,
    (b) displacing radially central layers of the absorbent material from the withdrawal end of the pledget towards the insertion end, to produce an increase in fiber density in at least some locations along an axially-extending central region of the tampon as compared to fiber density in regions radially outside of the central region,
    (c) radially compressing the pledget, and
    (d) forming an indentation in said withdrawal end of said pledget, wherein said withdrawal end is shaped to permit the user to apply an axial force thereto for inserting said tampon.

2. A method of forming a tampon intended for digital insertion, said tampon having an axial dimension oriented in an axial direction, a radial dimension oriented in a radial direction, an insertion end dimensioned for insertion into a body cavity, a withdrawal end, and a cord attached thereto for withdrawal from the cavity, said method comprising the steps of:
    (a) rolling a length of compressible absorbent material into a rolled layered pledget with one end corresponding to the withdrawal end and another end corresponding to the insertion end,
    (b) displacing radially central layers of the absorbent material from the withdrawal end of the pledget towards the insertion end, to produce an increase in fiber density in at least some locations along an axially-extending central region of the tampon as compared to fiber density in regions radially outside of the central region,
    (c) radially compressing the pledget, and
    (d) forming an indentation in said withdrawal end of said pledget, wherein said withdrawal end is shaped to permit the user to apply an axial force thereto for inserting said tampon, and wherein said indentation is formed by a pushrod having an elongated, substantially conical member extending from a substantially hemispherical base.

3. The method of claim 2 wherein the pushrod, in addition to forming the indentation, urges the compressed pledget against a head forming die.

4. The method of claim 2 further comprising the step of applying a permeable overwrap material to the pledget prior to compression.

5. A method of claim 4 wherein the overwrap material is applied in the form of an envelope having a bottom end wall and a tubular wall which surrounds at least a portion of the surface of the pledget.

6. A method of claim 5 wherein said overwrap material is applied so that the bottom end wall is adjacent the withdrawal end of the pledget.

7. A method of claim 6 wherein, after radial compression, excess overwrap material forming the bottom end wall is tucked into the indentation.

* * * * *